(12) United States Patent
Keyer et al.

(10) Patent No.: US 8,992,576 B2
(45) Date of Patent: Mar. 31, 2015

(54) POSTERIOR SPINE DYNAMIC STABILIZER

(75) Inventors: Tom Keyer, West Chester, PA (US); Eric McDivitt, Schwenksville, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1298 days.

(21) Appl. No.: 12/640,543

(22) Filed: Dec. 17, 2009

(65) Prior Publication Data

US 2010/0152776 A1    Jun. 17, 2010

Related U.S. Application Data

(60) Provisional application No. 61/138,450, filed on Dec. 17, 2008.

(51) Int. Cl.
| | | |
|---|---|---|
| *A61B 17/88* | (2006.01) | |
| *A61B 17/70* | (2006.01) | |
| *A61B 19/00* | (2006.01) | |

(52) U.S. Cl.
CPC .......... *A61B 17/7032* (2013.01); *A61B 17/7031* (2013.01); *A61B 17/7037* (2013.01); *A61B 17/7046* (2013.01); *A61B 17/705* (2013.01); *A61B 2019/304* (2013.01)
USPC ....................................... 606/257

(58) Field of Classification Search
USPC .............................. 606/250–279
See application file for complete search history.

(56) References Cited

U.S. PATENT DOCUMENTS

| | | | |
|---|---|---|---|
| 1,276,117 A | 8/1918 | Riebe | |
| 1,985,427 A | 12/1934 | Richardson | |
| 2,314,197 A | 3/1943 | Miller | |
| 2,379,577 A | 7/1945 | Harsted | |
| 2,546,026 A | 3/1951 | Coon | |
| 2,554,708 A | 5/1951 | Johannes | |
| 2,805,441 A | 9/1957 | Leon | |
| 2,845,748 A | 8/1958 | Derham | |
| 2,895,594 A | 7/1959 | Smith | |
| 2,995,151 A | 8/1961 | Lockwood | |
| 3,019,552 A | 2/1962 | Schleich | |
| 3,028,291 A | 4/1962 | Roberts et al. | |
| 3,325,327 A | 6/1967 | Swan | |
| 3,401,607 A | 9/1968 | Wortman | |

(Continued)

FOREIGN PATENT DOCUMENTS

| | | |
|---|---|---|
| CA | 2600672 | 9/2006 |
| DE | 2821678 | 11/1979 |

(Continued)

OTHER PUBLICATIONS

International Patent Application No. PCT/US2009/068464: International Search Report dated Apr. 14, 2010, 6 pages.

(Continued)

*Primary Examiner* — Mary Hoffman
*Assistant Examiner* — Tara Carter
(74) *Attorney, Agent, or Firm* — Baker & Hostetler LLP

(57) ABSTRACT

A dynamic stabilization system may include an elongated spinal rod, at least two bone anchors attached to the elongated rod, and a dynamic member. One of the bone anchors allows translation of the spinal rod with respect to the bone anchor. The dynamic member comprises a body and an elastomeric element coupled to at least one side of the body. The body of the element is capable of being attached to the elongated spinal rod between the two bone anchors.

12 Claims, 10 Drawing Sheets

(56) References Cited

U.S. PATENT DOCUMENTS

| | | | |
|---|---|---|---|
| 3,575,194 A | 4/1971 | McMurry | |
| 3,635,233 A | 1/1972 | Robertson | |
| 3,669,133 A | 6/1972 | Hyman | |
| 3,715,454 A | 2/1973 | Kleykmp | |
| 3,858,578 A | 1/1975 | Milo | |
| 4,041,939 A | 8/1977 | Hall | |
| 4,047,523 A | 9/1977 | Hall | |
| 4,369,769 A | 1/1983 | Edwards | |
| 4,378,712 A | 4/1983 | Yoshifuji | |
| 4,409,968 A | 10/1983 | Drummond | |
| 4,422,451 A | 12/1983 | Kalamchi | |
| 4,448,191 A | 5/1984 | Rodnyansky et al. | |
| 4,483,562 A | 11/1984 | Schoolman | |
| 4,569,338 A * | 2/1986 | Edwards | 606/278 |
| RE32,650 E | 4/1988 | Waddell | |
| 4,743,260 A | 5/1988 | Burton | |
| 4,773,402 A | 9/1988 | Asher et al. | |
| 4,911,346 A | 3/1990 | Shallman | |
| 4,932,975 A | 6/1990 | Main et al. | |
| 4,949,927 A | 8/1990 | Madocks et al. | |
| 4,960,410 A | 10/1990 | Pinchuk | |
| 4,979,531 A | 12/1990 | Toor et al. | |
| 4,987,892 A * | 1/1991 | Krag et al. | 606/264 |
| 5,002,576 A | 3/1991 | Fuhrmann et al. | |
| 5,011,497 A | 4/1991 | Persson et al. | |
| 5,029,847 A | 7/1991 | Ross | |
| 5,030,220 A | 7/1991 | Howland | |
| 5,055,104 A | 10/1991 | Ray | |
| 5,084,048 A | 1/1992 | Jacob et al. | |
| 5,092,867 A | 3/1992 | Harms et al. | |
| 5,133,716 A | 7/1992 | Plaza | |
| 5,180,393 A | 1/1993 | Commarmond | |
| 5,194,678 A | 3/1993 | Kramer | |
| 5,215,338 A | 6/1993 | Kimura et al. | |
| 5,246,442 A | 9/1993 | Ashman et al. | |
| 5,251,611 A | 10/1993 | Zehel et al. | |
| 5,254,118 A * | 10/1993 | Mirkovic | 606/264 |
| 5,261,908 A | 11/1993 | Campbell, Jr. | |
| 5,282,863 A | 2/1994 | Burton | |
| 5,353,843 A | 10/1994 | Hoag | |
| 5,375,823 A | 12/1994 | Navas | |
| 5,387,213 A | 2/1995 | Breard et al. | |
| 5,413,576 A | 5/1995 | Rivard | |
| 5,415,661 A | 5/1995 | Holmes | |
| 5,423,816 A | 6/1995 | Lin | |
| 5,423,820 A | 6/1995 | Miller et al. | |
| 5,468,241 A | 11/1995 | Metz-Stavenhagen et al. | |
| 5,480,401 A | 1/1996 | Navas | |
| 5,486,174 A | 1/1996 | Fournet-Fayard et al. | |
| 5,488,761 A | 2/1996 | Leone | |
| 5,507,812 A | 4/1996 | Moore | |
| 5,536,268 A | 7/1996 | Griss | |
| 5,540,688 A | 7/1996 | Navas | |
| 5,562,660 A | 10/1996 | Grob | |
| 5,562,737 A | 10/1996 | Graf | |
| 5,573,520 A | 11/1996 | Schwartz et al. | |
| 5,649,925 A | 7/1997 | Barbera Alacreu | |
| 5,658,286 A | 8/1997 | Sava | |
| 5,662,300 A | 9/1997 | Michelson | |
| 5,662,651 A | 9/1997 | Tornier et al. | |
| 5,672,175 A | 9/1997 | Martin | |
| 5,681,311 A | 10/1997 | Foley et al. | |
| 5,688,275 A | 11/1997 | Koros et al. | |
| 5,713,900 A | 2/1998 | Benzel et al. | |
| 5,725,582 A | 3/1998 | Bevan et al. | |
| 5,733,284 A | 3/1998 | Martin | |
| 5,814,046 A | 9/1998 | Hopf | |
| RE36,221 E | 6/1999 | Breard et al. | |
| 5,938,663 A | 8/1999 | Petreto | |
| 5,944,719 A | 8/1999 | Leban | |
| 5,964,767 A | 10/1999 | Tapia et al. | |
| 6,015,409 A | 1/2000 | Jackson | |
| 6,053,922 A | 4/2000 | Krause et al. | |
| 6,099,528 A | 8/2000 | Saurat | |
| 6,102,912 A | 8/2000 | Cazin et al. | |
| 6,162,223 A | 12/2000 | Orsak et al. | |
| 6,171,311 B1 * | 1/2001 | Richelsoph | 606/252 |
| 6,175,758 B1 | 1/2001 | Kambin | |
| 6,187,000 B1 | 2/2001 | Davison et al. | |
| 6,193,720 B1 | 2/2001 | Yuan et al. | |
| 6,241,730 B1 | 6/2001 | Alby | |
| 6,267,764 B1 | 7/2001 | Elberg | |
| 6,290,700 B1 | 9/2001 | Schmotzer | |
| 6,293,949 B1 | 9/2001 | Justis et al. | |
| 6,296,644 B1 | 10/2001 | Saurat et al. | |
| 6,337,142 B2 | 1/2002 | Harder et al. | |
| 6,355,038 B1 | 3/2002 | Pisharodi | |
| 6,402,750 B1 | 6/2002 | Atkinson et al. | |
| 6,440,169 B1 | 8/2002 | Elberg et al. | |
| 6,447,518 B1 | 9/2002 | Krause et al. | |
| 6,447,546 B1 | 9/2002 | Bramlet et al. | |
| 6,475,220 B1 | 11/2002 | Whiteside | |
| 6,475,242 B1 | 11/2002 | Bramlet | |
| 6,488,682 B2 | 12/2002 | Kikuchi et al. | |
| 6,520,495 B1 | 2/2003 | Le Mendola | |
| 6,530,934 B1 | 3/2003 | Jacobsen et al. | |
| 6,554,831 B1 | 4/2003 | Rivard et al. | |
| 6,575,979 B1 | 6/2003 | Cragg | |
| 6,576,018 B1 | 6/2003 | Holt | |
| 6,585,769 B1 | 7/2003 | Muhanna et al. | |
| 6,589,246 B1 | 7/2003 | Hack et al. | |
| 6,626,905 B1 | 9/2003 | Schmiel et al. | |
| 6,626,909 B2 | 9/2003 | Chin | |
| 6,645,207 B2 | 11/2003 | Dixon et al. | |
| 6,652,585 B2 | 11/2003 | Lange | |
| 6,682,533 B1 | 1/2004 | Dinsdale et al. | |
| 6,706,044 B2 | 3/2004 | Kuslich et al. | |
| 6,736,817 B2 * | 5/2004 | Troxell et al. | 606/252 |
| 6,749,614 B2 | 6/2004 | Teitelbaum et al. | |
| 6,783,527 B2 | 8/2004 | Drewry et al. | |
| 6,827,743 B2 | 12/2004 | Eisermann et al. | |
| 6,835,205 B2 | 12/2004 | Atkinson et al. | |
| 6,884,241 B2 | 4/2005 | Bertranou et al. | |
| 6,966,910 B2 | 11/2005 | Ritland | |
| 6,986,771 B2 | 1/2006 | Paul et al. | |
| 6,989,011 B2 | 1/2006 | Paul et al. | |
| 7,083,621 B2 | 8/2006 | Shaolian et al. | |
| 7,094,237 B2 | 8/2006 | Gradel et al. | |
| 7,097,648 B1 | 8/2006 | Globerman et al. | |
| 7,125,410 B2 | 10/2006 | Freudiger | |
| 7,137,985 B2 | 11/2006 | Jahng | |
| 7,229,441 B2 | 6/2007 | Trieu et al. | |
| 7,326,210 B2 | 2/2008 | Jahng et al. | |
| 7,329,258 B2 | 2/2008 | Studer | |
| 7,335,200 B2 | 2/2008 | Carli | |
| 7,377,921 B2 | 5/2008 | Studer et al. | |
| 7,556,639 B2 | 7/2009 | Rothman et al. | |
| 7,611,518 B2 | 11/2009 | Walder et al. | |
| 7,717,941 B2 | 5/2010 | Petit | |
| 7,763,052 B2 | 7/2010 | Jahng | |
| 7,815,665 B2 | 10/2010 | Jahng et al. | |
| 8,029,546 B2 * | 10/2011 | Capote et al. | 606/257 |
| 2001/0020169 A1 | 9/2001 | Metz-Stavenhagen | |
| 2001/0037111 A1 | 11/2001 | Dixon et al. | |
| 2001/0049559 A1 | 12/2001 | Koo et al. | |
| 2002/0010467 A1 | 1/2002 | Cooper et al. | |
| 2002/0035366 A1 | 3/2002 | Walder et al. | |
| 2002/0049394 A1 | 4/2002 | Roy et al. | |
| 2002/0055740 A1 | 5/2002 | Lieberman | |
| 2002/0065557 A1 | 5/2002 | Goble et al. | |
| 2002/0082600 A1 | 6/2002 | Shaolian et al. | |
| 2002/0087159 A1 | 7/2002 | Thomas | |
| 2002/0095154 A1 | 7/2002 | Atkinson et al. | |
| 2002/0099378 A1 | 7/2002 | Michelson | |
| 2002/0107570 A1 | 8/2002 | Sybert et al. | |
| 2002/0111628 A1 | 8/2002 | Ralph et al. | |
| 2002/0111630 A1 | 8/2002 | Ralph et al. | |
| 2002/0120270 A1 | 8/2002 | Trieu et al. | |
| 2002/0123668 A1 | 9/2002 | Ritland | |
| 2002/0123750 A1 | 9/2002 | Eisermann et al. | |
| 2002/0123806 A1 | 9/2002 | Reiley | |
| 2002/0133155 A1 | 9/2002 | Ferree | |
| 2002/0138077 A1 | 9/2002 | Ferree | |
| 2002/0143329 A1 | 10/2002 | Serhan et al. | |

(56) References Cited

U.S. PATENT DOCUMENTS

| | | |
|---|---|---|
| 2002/0143401 A1 | 10/2002 | Michelson |
| 2002/0169450 A1 | 11/2002 | Lange |
| 2002/0183748 A1 | 12/2002 | Martin et al. |
| 2002/0198526 A1 | 12/2002 | Shaolian et al. |
| 2003/0028192 A1* | 2/2003 | Schar et al. ............... 606/61 |
| 2003/0032958 A1 | 2/2003 | Soubeiran |
| 2003/0040746 A1 | 2/2003 | Mitchell et al. |
| 2003/0040797 A1 | 2/2003 | Fallin et al. |
| 2003/0045875 A1 | 3/2003 | Bertranou et al. |
| 2003/0055426 A1 | 3/2003 | Carbone et al. |
| 2003/0060823 A1 | 3/2003 | Bryan |
| 2003/0073998 A1 | 4/2003 | Pagliuca et al. |
| 2003/0083657 A1 | 5/2003 | Drewry et al. |
| 2003/0083688 A1 | 5/2003 | Simonson |
| 2003/0088251 A1 | 5/2003 | Braun et al. |
| 2003/0093078 A1 | 5/2003 | Ritland |
| 2003/0109880 A1 | 6/2003 | Shirado et al. |
| 2003/0171749 A1 | 9/2003 | Le Couedic et al. |
| 2003/0191371 A1 | 10/2003 | Smith et al. |
| 2003/0191470 A1 | 10/2003 | Ritland |
| 2003/0195514 A1 | 10/2003 | Trieu et al. |
| 2003/0195551 A1 | 10/2003 | Davison et al. |
| 2003/0220643 A1 | 11/2003 | Ferree |
| 2004/0002708 A1 | 1/2004 | Ritland |
| 2004/0049189 A1 | 3/2004 | Le Couedic et al. |
| 2004/0049190 A1 | 3/2004 | Biedermann et al. |
| 2004/0138661 A1 | 7/2004 | Bailey |
| 2004/0138662 A1 | 7/2004 | Landry et al. |
| 2004/0143264 A1 | 7/2004 | McAfee |
| 2004/0147928 A1 | 7/2004 | Landry et al. |
| 2004/0172025 A1 | 9/2004 | Drewry et al. |
| 2004/0215191 A1 | 10/2004 | Kitchen |
| 2004/0215193 A1 | 10/2004 | Shaolian et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0267260 A1 | 12/2004 | Mack et al. |
| 2005/0021029 A1 | 1/2005 | Trieu et al. |
| 2005/0033295 A1 | 2/2005 | Wisnewski |
| 2005/0033299 A1 | 2/2005 | Shluzas |
| 2005/0038432 A1 | 2/2005 | Shaolian et al. |
| 2005/0049708 A1 | 3/2005 | Atkinson et al. |
| 2005/0065514 A1 | 3/2005 | Studer |
| 2005/0065516 A1 | 3/2005 | Jahng |
| 2005/0085815 A1 | 4/2005 | Harms et al. |
| 2005/0090822 A1 | 4/2005 | DiPoto |
| 2005/0101957 A1 | 5/2005 | Buskirk et al. |
| 2005/0113927 A1 | 5/2005 | Malek |
| 2005/0124991 A1 | 6/2005 | Jahng |
| 2005/0131407 A1 | 6/2005 | Sicvol et al. |
| 2005/0154390 A1 | 7/2005 | Biedermann et al. |
| 2005/0165396 A1 | 7/2005 | Fortin et al. |
| 2005/0171539 A1 | 8/2005 | Braun et al. |
| 2005/0171540 A1 | 8/2005 | Lim et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0182401 A1 | 8/2005 | Timm et al. |
| 2005/0182409 A1 | 8/2005 | Callahan et al. |
| 2005/0203511 A1 | 9/2005 | Wilson-MacDonald et al. |
| 2005/0203513 A1 | 9/2005 | Jahng et al. |
| 2005/0203517 A1 | 9/2005 | Jahng et al. |
| 2005/0203519 A1 | 9/2005 | Harms et al. |
| 2005/0222569 A1 | 10/2005 | Panjabi |
| 2005/0228381 A1 | 10/2005 | Kirschman |
| 2005/0245930 A1 | 11/2005 | Timm et al. |
| 2005/0261682 A1 | 11/2005 | Ferree |
| 2005/0261685 A1 | 11/2005 | Fortin et al. |
| 2005/0261686 A1 | 11/2005 | Paul |
| 2005/0277922 A1 | 12/2005 | Trieu et al. |
| 2005/0288670 A1 | 12/2005 | Panjabi et al. |
| 2005/0288672 A1 | 12/2005 | Ferree |
| 2006/0009768 A1 | 1/2006 | Ritland |
| 2006/0015100 A1 | 1/2006 | Panjabi et al. |
| 2006/0036240 A1* | 2/2006 | Colleran et al. ............... 606/61 |
| 2006/0036244 A1* | 2/2006 | Spitler et al. ............... 606/61 |
| 2006/0084982 A1 | 4/2006 | Kim |
| 2006/0111715 A1 | 5/2006 | Jackson |
| 2006/0129147 A1 | 6/2006 | Biedermann et al. |
| 2006/0142758 A1 | 6/2006 | Petit |
| 2006/0142760 A1 | 6/2006 | McDonnell |
| 2006/0149238 A1 | 7/2006 | Sherman et al. |
| 2006/0189983 A1 | 8/2006 | Fallin et al. |
| 2006/0189984 A1 | 8/2006 | Fallin et al. |
| 2006/0212033 A1 | 9/2006 | Rothman et al. |
| 2006/0229612 A1 | 10/2006 | Rothman et al. |
| 2006/0240533 A1 | 10/2006 | Sengupta et al. |
| 2006/0241594 A1 | 10/2006 | McCarthy et al. |
| 2006/0247626 A1* | 11/2006 | Taylor et al. ............... 606/61 |
| 2006/0260483 A1 | 11/2006 | Hartmann et al. |
| 2006/0264940 A1 | 11/2006 | Hartmann |
| 2006/0293657 A1 | 12/2006 | Hartmann |
| 2007/0016193 A1 | 1/2007 | Ritland |
| 2007/0073293 A1 | 3/2007 | Martz et al. |
| 2007/0118122 A1 | 5/2007 | Butler et al. |
| 2007/0123864 A1 | 5/2007 | Walder et al. |
| 2007/0123865 A1 | 5/2007 | Schlapfer et al. |
| 2007/0129729 A1 | 6/2007 | Petit et al. |
| 2007/0149909 A1 | 6/2007 | Fortin et al. |
| 2007/0198088 A1 | 8/2007 | Biedermann et al. |
| 2008/0065079 A1 | 3/2008 | Bruneau et al. |
| 2008/0195149 A1 | 8/2008 | Burke |
| 2008/0195154 A1 | 8/2008 | Brown et al. |
| 2009/0105763 A1* | 4/2009 | Kirschman ............... 606/264 |

FOREIGN PATENT DOCUMENTS

| | | |
|---|---|---|
| DE | 4109941 | 10/1992 |
| DE | 4239716 | 8/1994 |
| DE | 19746687 | 5/1999 |
| DE | 10348329 B3 | 2/2005 |
| EP | 0677277 | 3/1995 |
| EP | 0669109 | 8/1995 |
| EP | 1677689 A2 | 7/2006 |
| FR | 2702363 | 3/1993 |
| FR | 2694182 A1 | 2/1994 |
| FR | 2715825 A1 | 8/1995 |
| FR | 2717370 | 9/1995 |
| FR | 2718946 | 10/1995 |
| FR | 2728158 | 6/1996 |
| FR | 2775583 A1 | 9/1999 |
| FR | 2799949 | 4/2001 |
| GB | 2382304 | 5/2003 |
| JP | 07-008504 | 1/1995 |
| JP | 09108247 | 4/1997 |
| JP | 2000-325358 | 11/2000 |
| JP | 2002224131 | 8/2002 |
| JP | 200325358 | 2/2003 |
| WO | WO 95/05785 | 3/1995 |
| WO | WO 01/28436 | 4/2001 |
| WO | WO 2004/017817 | 3/2004 |
| WO | WO 2004/069987 | 8/2004 |
| WO | WO 2004/098452 A2 | 11/2004 |
| WO | WO 2004/105577 | 12/2004 |
| WO | WO 2005/030031 | 4/2005 |
| WO | WO 2005/044117 | 5/2005 |
| WO | WO 2005/039454 | 6/2005 |
| WO | WO 2005/092222 | 10/2005 |
| WO | WO 2005/094704 | 10/2005 |
| WO | WO 2005/110257 | 11/2005 |
| WO | WO 2006/063107 | 6/2006 |
| WO | WO 2006/096414 | 9/2006 |
| WO | WO 2008/100944 | 8/2008 |
| WO | WO 2010/078029 | 7/2010 |

OTHER PUBLICATIONS

International Patent Application No. PCT/US2009/068464: International Preliminary Report on Patentability dated Jan. 14, 2011, 15 pages.

Kanayma et al., Journal of Neurosurgery, 2001, 95(Spine1), 5-10.

(56) References Cited

OTHER PUBLICATIONS

Mullholland et al., European Spine Journal, 2002, 11(Suppl. 2), S198-205.
Schmoelz et al., "Dynamic Stabilization of the Lumbar Spine and its effects on Adjacent Segments: An In Vitro Experiment", Journal of Spinal Disorders & Techniques, Aug. 2003, 16(4), 418-423.
Markwalder et al., "Dynamic Stabilization of Lumbar Motion Segments by Use of Graf's Ligaments with an Average Follow-Up of 7.4 years in 39 Highly selected Consecutive Patients", Acta Neurochirurgica, 2003, 145(3), 209-214.
Stoll et al., "The Dynamic Neutralization System for the Spine: A Multi-Center Study of a Novel non-fusion System", European Spine Journal, 11(Suppl 2), 2002, S170-178.

* cited by examiner

POSTERIOR SPINE DYNAMIC STABILIZER

CROSS REFERENCE TO RELATED APPLICATIONS

This application claims priority to U.S. Provisional Application No. 61/138,450, filed Dec. 17, 2008, the contents of which are incorporated herein in their entirety.

BACKGROUND

Patients who have a lumbar spinal fusion have an increased risk of having adjacent segment disease. Adjacent segment disease occurs after the spinal fusion in which the segment or the intervertebral disc and the facet joints are degenerated at the adjacent level above or below the lumbar fusion.

Often, a disorder in one spinal component can lead to ultimate disorder in an adjacent component of the spine. In such cases, both components will ultimately require a spinal fusion. However, if the adjacent spinal component (that is partially diseased) is fused with the fully diseased component, the patient will not only lose more mobility in the spine, but the partially diseased component will degrade quicker. Thus it may be desired to not fully immobilize the adjacent spinal component that is only partially diseased.

SUMMARY

A dynamic stabilization system in accordance with one embodiment may include an elongated spinal rod, at least two bone anchors attached to the elongated rod, and a dynamic member. One of the bone anchors allows translation of the spinal rod with respect to the bone anchor. The dynamic member comprises a body and an elastomeric element coupled to at least one side of the body. The body is capable of being attached to the elongated spinal rod between the two bone anchors.

A dynamic stabilization member constructed in accordance with one embodiment may include a body, an elastomeric element attached to at least one side of the body, a collet retained in the body, and a locking cap extending through the body and into a bore of the collet. The bore of the collet defines internal thread. The locking cap may have external threads that engage the internal threads of the collet. The collet may be capable of receiving a spinal rod between a pair of bone anchors, and may be capable of clamping to the spinal rod upon threaded advancement of the locking cap.

BRIEF DESCRIPTION OF THE DRAWINGS

Several embodiments of the invention will be described in the following by way of example and with reference to the accompanying drawings in which.

DETAILED DESCRIPTION OF ILLUSTRATIVE EMBODIMENTS

Figure 1:
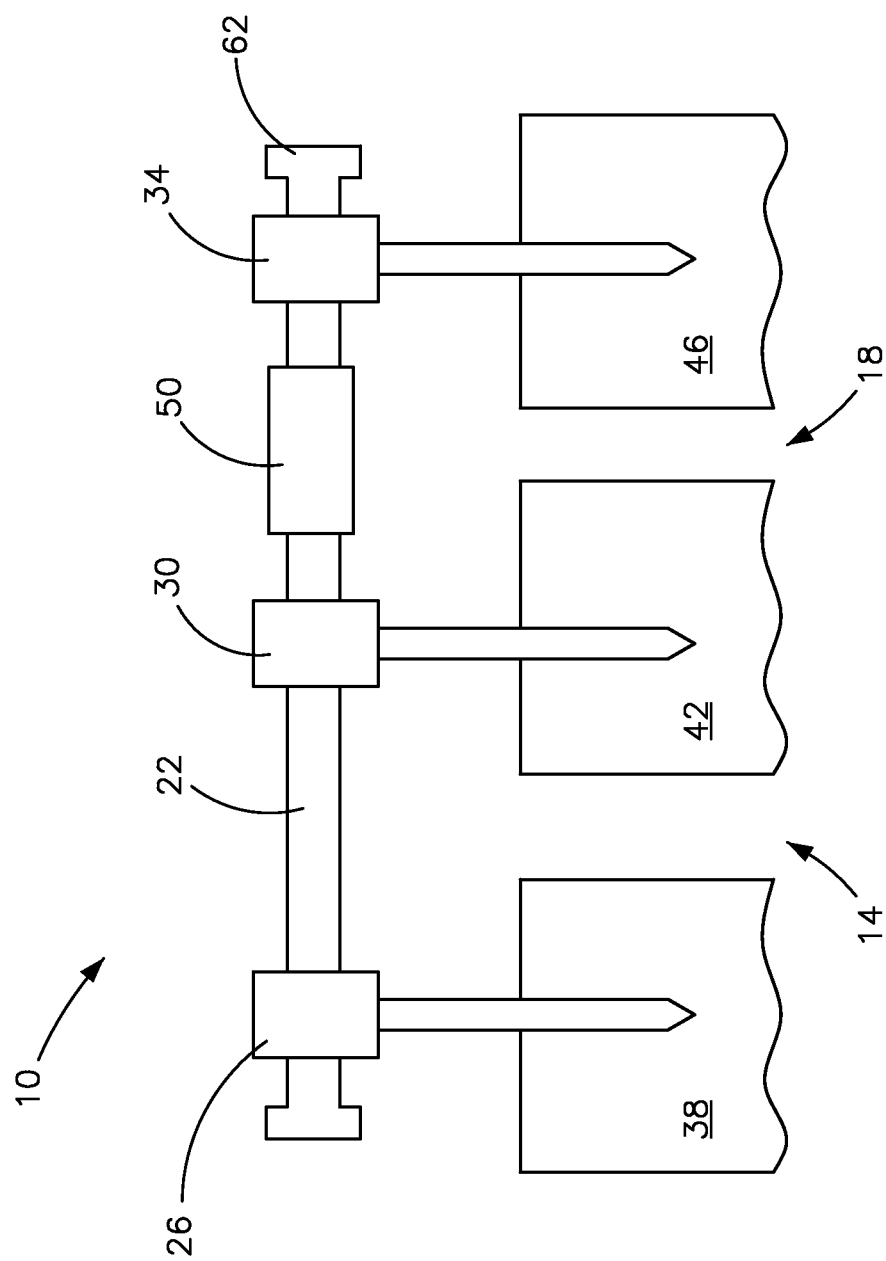
FIG. 1 is a schematic side view of a dynamic stabilization system according to an embodiment of the invention.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the dynamic stabilization system and related parts thereof. The words, "anterior", "posterior", "superior," "inferior", "lateral" and related words and/or phrases designate preferred positions and orientations in the human body to which reference is made and are not meant to be limiting. The terminology includes the above-listed words, derivatives thereof and words of similar import.

FIG. 1 generally shows a dynamic stabilization system 10 spanning a static fusion level 14 of a patient's spine and a non-fusion level 18 adjacent to the static fusion level 14. As shown, the dynamic stabilization system 10 includes a spinal rod 22 spanning the static fusion level 14 and the non-fusion level 18. The spinal rod 22 is secured to the spine via bone anchors, such as pedicle screw assemblies 26, 30, and 34 that are each mounted to respective vertebral bodies 38, 42, and 46. A dynamic member 50 is attached to the spinal rod 22 between pedicle screw assemblies 30, and 34. Dynamic member 50 allows the non-fusion level 18 to have some mobility while the fusion level 14 is completely immobilized.

The spinal rod 22 is generally a rigid elongated rod used for spinal corrective surgery and may be made from titanium, stainless steel, or other biocompatible, generally rigid materials. Spinal rod 22 may include flares 62 at each end. Flares 62 may operate as stops to limit and generally prevent over translation of spinal rod 22 with respect to the third pedicle screw assembly 34.

Pedicle screw assemblies 26, and 30 may be any conventional monaxial or polyaxial pedicle screw or lamina hook assemblies known in the art, and can be bottom loading (in which the bone anchor is inserted into an anchor seat through the bottom of the assembly) or top loading (in which the bone anchor is dropped down through the assembly from the top). Pedicle screw assemblies 26, and 30 are configured to lock both the angulation of the bone anchor, as well as the translation or position of spinal rod 22 with respect to the pedicle screw assemblies 26, and 30. Pedicle screw assembly 34, on the other hand, is configured to lock the angulation of the bone anchor, while allowing translation of spinal rod 22 with respect to pedicle screw assembly 34 along a direction X.

Figure 2:
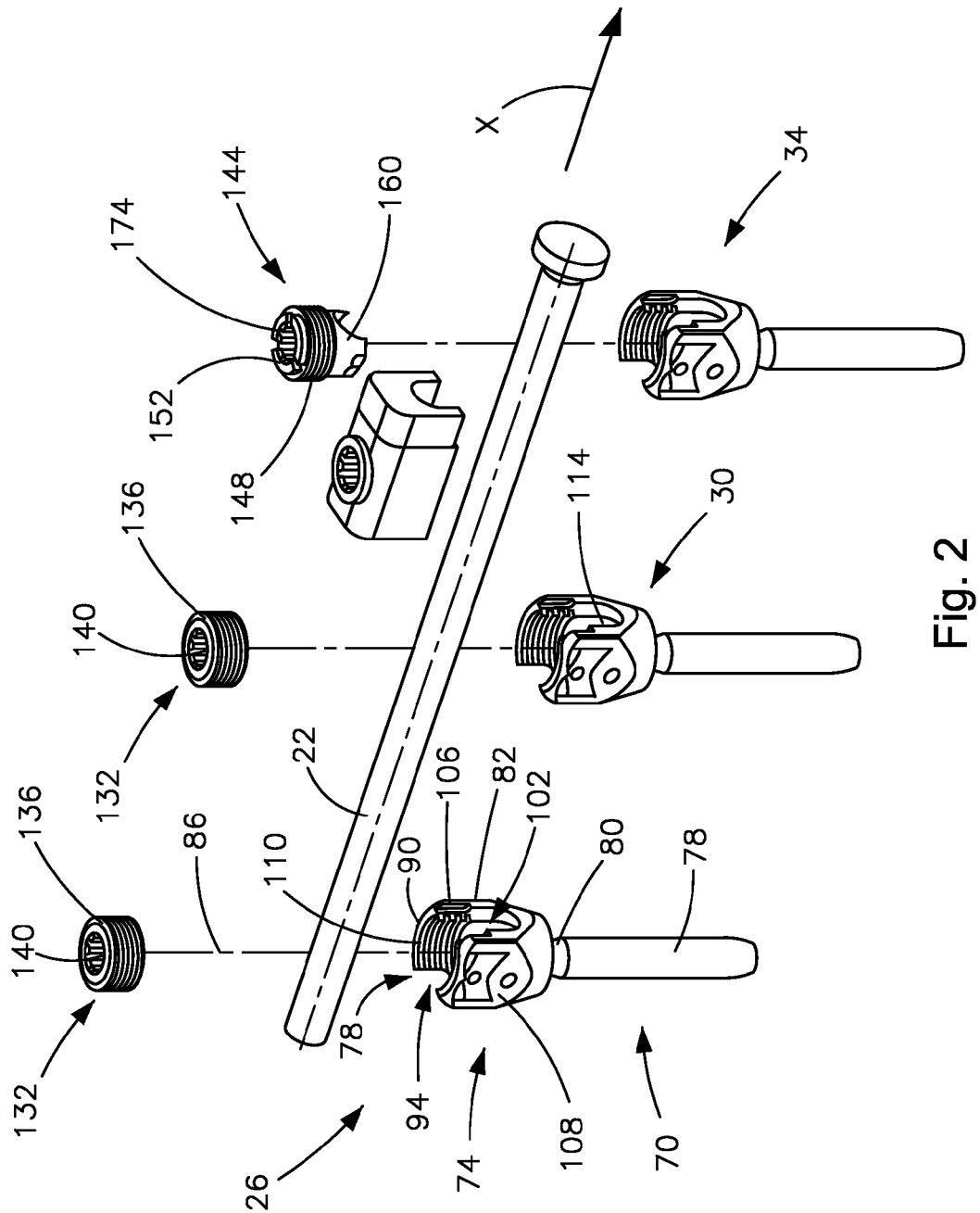
FIG. 2 is an exploded perspective view of a dynamic stabilation system.

As shown in FIG. 2, screw assemblies 26, 30, and 34 each include an anchor portion 70, and an anchor seat 74 mounted on the anchor portion 70. Anchor portion 70 includes an elongated threaded shaft 78 for engaging the patient's vertebra, such as vertebral bodies 38, 42, and 46 shown in FIG. 1, and a head 80.

Anchor seat 74, which is mounted on the head 80 (best shown in FIG. 3) of anchor portion 70 includes a body 82 which may be described as a cylindrical tubular body having a longitudinal axis 86, an upper end 90 having an opening 94, and an axial bore 98 that is substantially coaxial with the longitudinal axis 86 of the body 82. The axial bore 98 extends from opening 94 to a lower opening (not shown). Body 82 also includes a substantially transverse rod-receiving channel 102 (shown as a top loading U-shaped receiving channel) defining a pair of spaced apart arms 106, and 108. The inner surface of the spaced apart arms 106, 108 preferably include a plurality of threads 110 for engaging the cap. Contained within the axial bore 98 of body 82 is a collet 114 having a seat sized and configured to receive at least a portion of the spinal rod 22 when the spinal rod 22 is received within the rod-receiving channel 102 of body 82.

Figure 3:
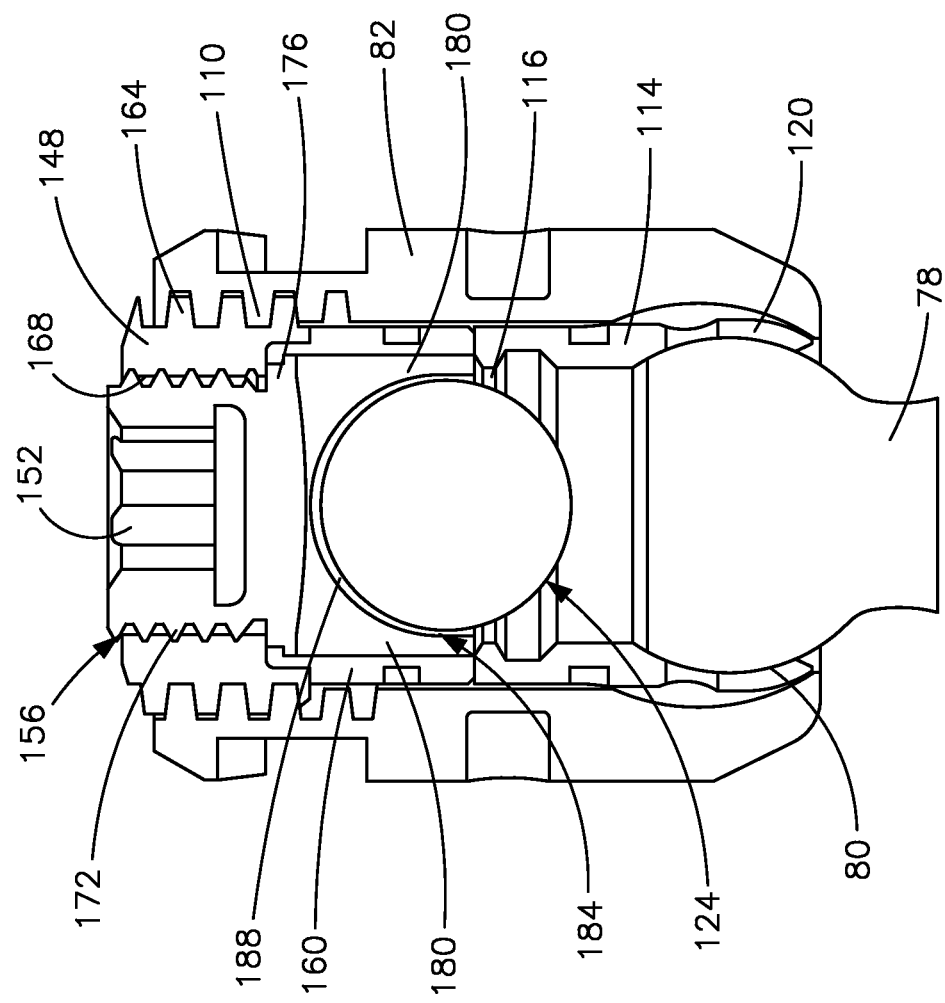
FIG. 3 is a front side cut away view of a bone anchor that allows translation of a spinal rod, after it has been fully assembled.

As best shown in FIG. 3, collet 114 includes a first or upper end 116 sized and configured to contact at least a portion of the spinal rod 22 when the spinal rod 22 is received within the rod-receiving channel 102 formed in the body 82, and a second or lower end 120 sized and configured to contact at least a portion of the head 80 of the anchor portion 70. Preferably, the upper end 116 of the collet 114 includes a seat 124 sized and configured to receive at least a portion of the spinal rod 22 when the spinal rod 22 is received within the rod-receiving channel 102 of the body 82. The lower end 120 of the collet 114 preferably includes an interior cavity 128 for receiving and securing the head 80 of the anchor portion 70, so that the anchor portion 70 can polyaxially rotate through a range of angles with respect to the collet 114 and hence with respect to the body 82.

Referring back to FIG. 2, each pedicle screw assembly 26, and 30 further includes a cap 132. Cap 132 is preferably an externally threaded set screw 136 for threadably engaging the threads 110 formed on the inner surface of body 82. Incorporation of a threaded screw 136 enables the set screw 136 to reduce the spinal rod 22 during tightening of the cap with respect to the body 82. It should be understood, however, that the cap 132 is not limited to a threaded set screw 136, and that other caps 132 may be used to reduce the spinal rod into the body of the pedicle screw.

As shown, cap 132 includes a drive surface 140 capable of being engaged by a corresponding drive tool for securing the cap 132 onto the body 82. The drive surface 140 may take on any form, including but not limited to, an external hexagon a star drive pattern, a Phillips head pattern, etc.

As best shown in FIGS. 2 and 3, pedicle screw assembly 34 includes a two-step locking cap assembly 144 that enables the spinal rod to translate when cap assembly 144 is tightened onto body 82. Cap assembly 144 includes an outer locking screw 148, in inner set screw 152 disposed within an axial bore 156 of the outer locking screw 148, and an extension 160 that extends down from the outer locking screw 148.

As best shown in FIG. 3, outer locking screw 148 includes external threads 164 for threadably engaging the threads 110 formed on the inner surface of body 82. Incorporation of threads 164 enables the outer locking screw 148 to reduce the cap assembly 144, and thus the spinal rod 22 during tightening of the cap assembly 144 with respect to the body 82. The axial bore 156 of outer locking screw 148 includes internal threads 168 for threadably engaging external threads 172 of inner set screw 152. Thus inner set screw 152 may be reduced with respect to both outer locking screw 148 and the body 82.

Inner set screw 152 further includes a drive surface 174 capable of being engaged by a corresponding drive tool, and a base 176 that extends from a lower end of the inner set screw 152. The drive tool may engage drive surface 174 to thereby reduce the inner set screw 152 within the outer locking screw 148. As inner set screw 152 is reduced, base 176 will contact spinal rod 22 thereby preventing translation of spinal rod 22 with respect to pedicle screw assembly 34. It should be understood that the drive surface 174 may take on any form, including but not limited to, an external hexagon a star drive pattern, a Phillips head pattern, etc.

Extension 160 extends down from outer locking screw 148 and includes two legs 180 that define a U-shaped channel 184 for receiving the spinal rod 22. As shown in FIG. 3, when legs 180 contact collet 114, channel 184 defines a space 188 between spinal rod 22 and an internal surface 192 of legs 180. The space 188 should be large enough to allow spinal rod 22 to translate within channel 184 with respect to the pedicle screw 34.

In operation, and in continuing reference to FIG. 3, the head 80 of the anchor portion 70 is inserted into the collet 114, e.g., by placing the anchor seat 74 and collet 114 over the head of a previously implanted anchor portion 70 and applying a downward pressure that forces the head 80 of the anchor portion 70 to pop into the collet 114. Alternatively, pedicle screw assembly 34, including the anchor portion 70, may be preassembled prior to the implantation of the anchor portion 70 into bone. To lock the angulation of the anchor portion 70 with respect to the anchor seat 74, the outer locking screw 148 is reduced along longitudinal axis 86, e.g., preferably using a driver instrument, with respect to the anchor seat 74 via the mating of the external threads 164 of the outer locking screw 148 and the internal threads 124 of the anchor seat 74. As the outer locking screw 148 is reduced within the anchor seat 74, the outer locking screw extension 160 engages and applies a downward force to the top of the collet 114, the result of which causes the exterior surface of the collet 114 to interact with the interior surface of the anchor seat 74, resulting in the collapsing of the collet 114 around the head 80 of the anchor portion 70 and the locking of the polyaxial angular freedom of the anchor portion 70 with respect to the anchor seat 74, or vice versa. In such a configuration, the angular freedom of the anchor portion 70 and anchor seat 74 are locked while the translational freedom of the rod 22 is permitted. The translational freedom of the spinal rod 22 with respect to the pedicle screw assembly 34 can be locked by advancing the inner set screw 152 with respect to the outer locking screw 148, e.g., preferably by using a driver instrument, to cause the base 176 of the inner set screw 152 to bear down against the top of the rod 22 and clamp the rod 22 between the base 176 of the inner set screw 152 and the top of the collet 114. The pedicle screw assembly 34 can also be used in lieu of the pedicle screw assemblies 26, and 30, a configuration which allows a surgeon to pick and choose which pedicle screw assemblies 26, 30, and 34 to allow translational freedom of the spinal rod 22 with respect to and which pedicle screw assemblies 26, 30, and 34 to lock the translational freedom of the spinal rod 22 with respect to. Such a scenario can be beneficial in a revision situation in which a surgeon can make the dynamic level rigid by simply creating a small incision and tightening the inner setscrew 152.

Alternatively, the outer locking screw extension 160 can be replaced by an upwardly extending collet extension, to serve the same purpose of locking the angulation of the anchor portion 70 while allowing translational freedom of the spinal rod 22. The outer locking screw extension 160 can also be replaced by an intermediate member that serves the same functionality, as would be apparent to one having ordinary skill in the art.

As shown in FIGS. 4A-4E, dynamic member 50 includes an elongated body 200, a collet 204 received within the body 200, and a set screw 208 extending into an axial bore 212 of the body 200. The body 200 generally includes a cavity 216 that opens up into a channel 218. The channel 218 is generally defined by two legs 220 that extend down from a top 224 of the body 200. The channel 216 is open at its bottom and extends through the body 200 along the same axis as the rod-receiving channels 102 of the pedicle screw assemblies. The legs 220 each include a taper 228 at their distal ends and have internal surfaces 230 that interface with the collet 204. The axial bore 212 extends through the top 224 of the body 200 and into an axial bore 236 of the collet 204 which is contained within the cavity 216 of the body 200.

Figure 4A:
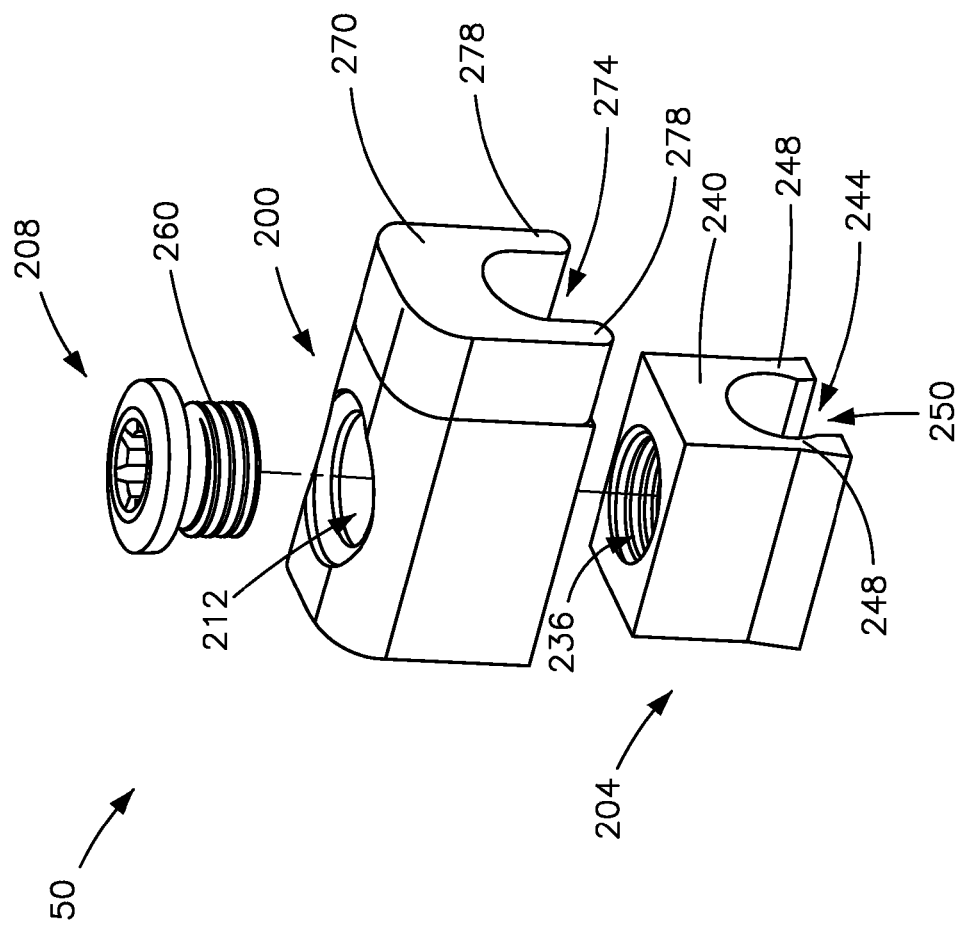
FIG. 4A is an exploded perspective view of a dynamic stabilizer according to an embodiment of the invention.
Figure 4B:
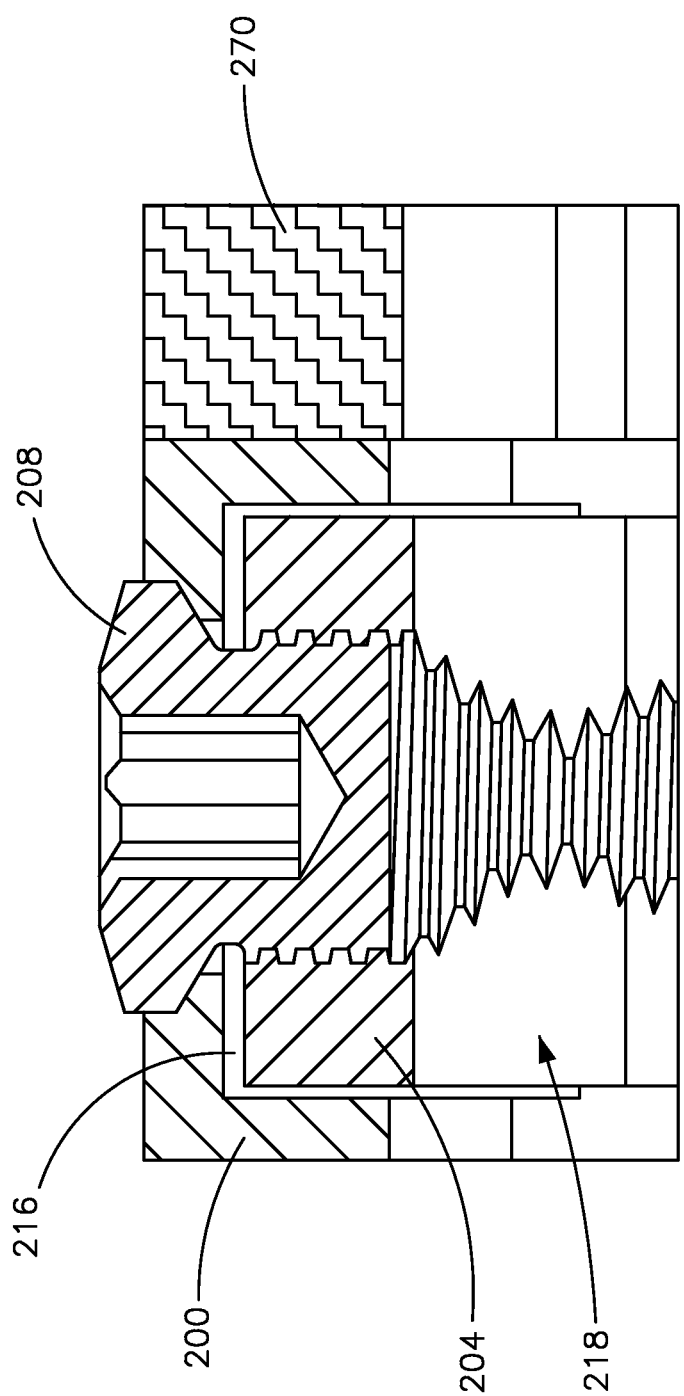
FIG. 4B is a left side cut away view of the fully assembled dynamic stabilier shown in FIG. 4A.

Collet 204 includes an elongated body 240 having a rod-receiving channel 244 defined by two downwardly extending legs 248. The channel 244 extends along the same axis as the rod-receiving channels 102 of the pedicle screw assemblies. Channel 244 is cylindrical and includes an opening 250 at its bottom. As shown in FIG. 4C, opening 250 is wider than the diameter of rod 22 before the member 50 is placed onto rod 22. Conversely, opening 250 is smaller than the diameter of rod 22, once member 50 has been tightened onto the rod 22, as shown in FIG. 4E. This is possible due to the interaction between the body 200 and the collet 204. It should be understood that the opening 250 may be smaller than the rod 22 before the member is place onto the rod 22. In such an embodiment the member may snap onto the rod 22.

Figure 4C:
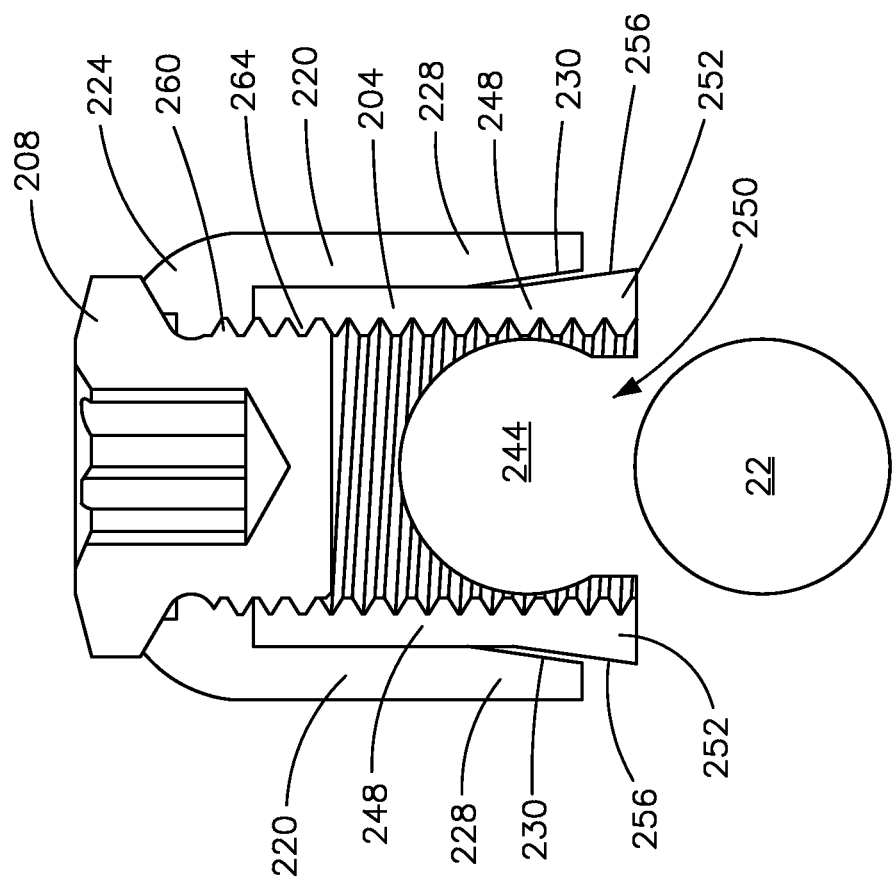
FIG. 4C is a front side cut away view of the fully assembled dynamic stabilizer shown in FIG. 4A prior to being attached to the spinal rod.
Figure 4D:
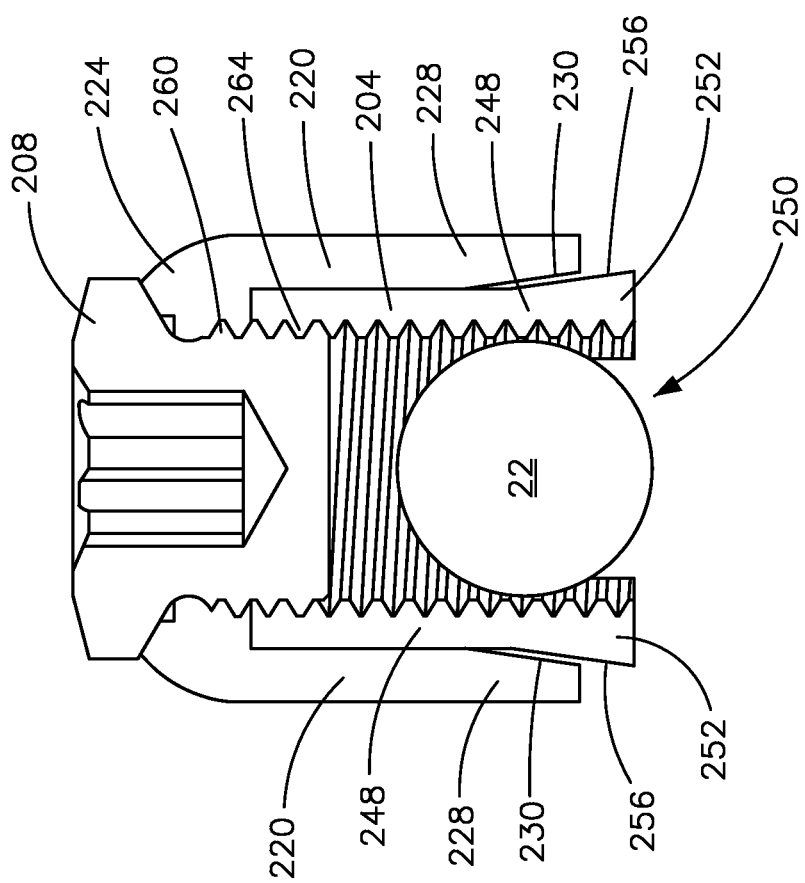
FIG. 4D is a front side cut away view of the fully assembled dynamic stabilizer shown in FIG. 4A attached to the spinal rod.
Figure 4E:
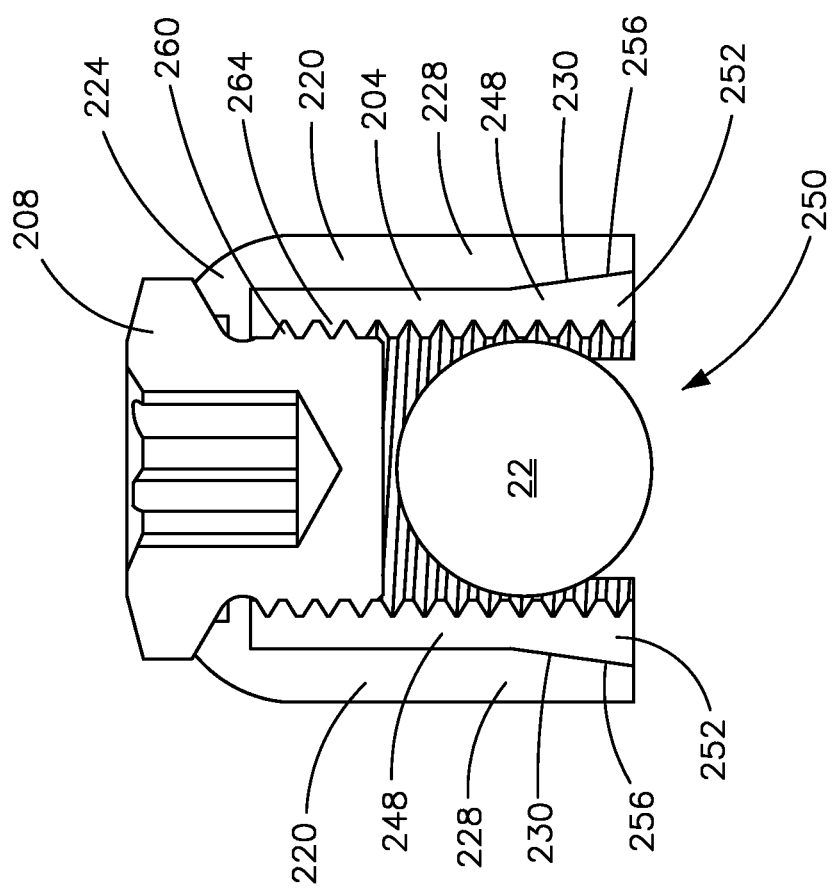
FIG. 4E is a front side cut away view of the fully assembled dynamic stabilizer shown in FIG. 4A tightened to the spinal rod.

For example, as shown in FIGS. 4C-4E, legs 248 of collet 204 each include an end portion 252 that gradually widens as the legs 248 extend distally. An outer surface 256 of each end portion 252 interfaces with a respective inner surface 230 of the legs 220 of body 200. As the collet 204 is brought further into the cavity 216 of body 200, the outer surfaces 256 of legs 248 begin to abut the inner surfaces 230 of the legs 220 of body 200. With further advancement of the collet 204 into the cavity 216, the legs 248 of the collet close around the rod 22, thereby tightening the member 50 to the rod 22. Member 50 is prevented from falling off of rod 22 because the opening 250 of the channel 244 is smaller than the diameter of the rod 22 once the collet 204 is fully advanced into the cavity 216.

Collet 204 is capable of being pulled into the cavity 216 because set screw 208 includes external threads 260 that engage internal threads 264 of the axial bore 236 of collet 204. Thus, as set screw 208 is rotated, collet 204 is pulled into cavity 216 of body 200. Alternatively, an externally threaded portion of the collet 204 can protrude above the body 200 and can be locked via a nut instead of the set screw 208. It should be understood that any locking cap may be used for tightening the member 50 to the spinal rod 22.

Member 50 further includes a stop member such as elastomeric element 270 that is attached to at least one side surface of the body 200. Elastomeric element 270 can assume a range of structures, geometries, and stiffnesses and may be constructed of nearly any biocompatible material having generally elastic or flexible properties. For example, elastomeric element 270 may be made from a PCU or PEU material that is over molded onto the body 200.

As shown in FIGS. 4A and 4B, elastomeric element 270 defines a rod-receiving channel 274 that extends into the rod receiving channel 244 of the collet 204. As shown, channel 274 is generally U-shaped, defining opposing legs 278. Elastomeric element 270 can serve as a bumper between the member 50 and the pedicle screw assembly 34. For example, as rod 22 is translated through pedicle screw assembly 34, translation will halt once elastomeric element 270 contacts pedicle screw assembly 34. Thus, member 50 may be positioned on rod 22 so as to limit translation of rod 22 with respect to pedicle screw assembly 34 to a desired length. It should be understood that elastomeric element 270 may be coupled to both side surfaces of body 200 to dampen motion of rod 22 relative to both pedicle screw assemblies 30 and 34. The member 50 can also be utilized in direct conjunction with an interbody fusion implant to provide load-sharing on the interbody device.

Figure 5:
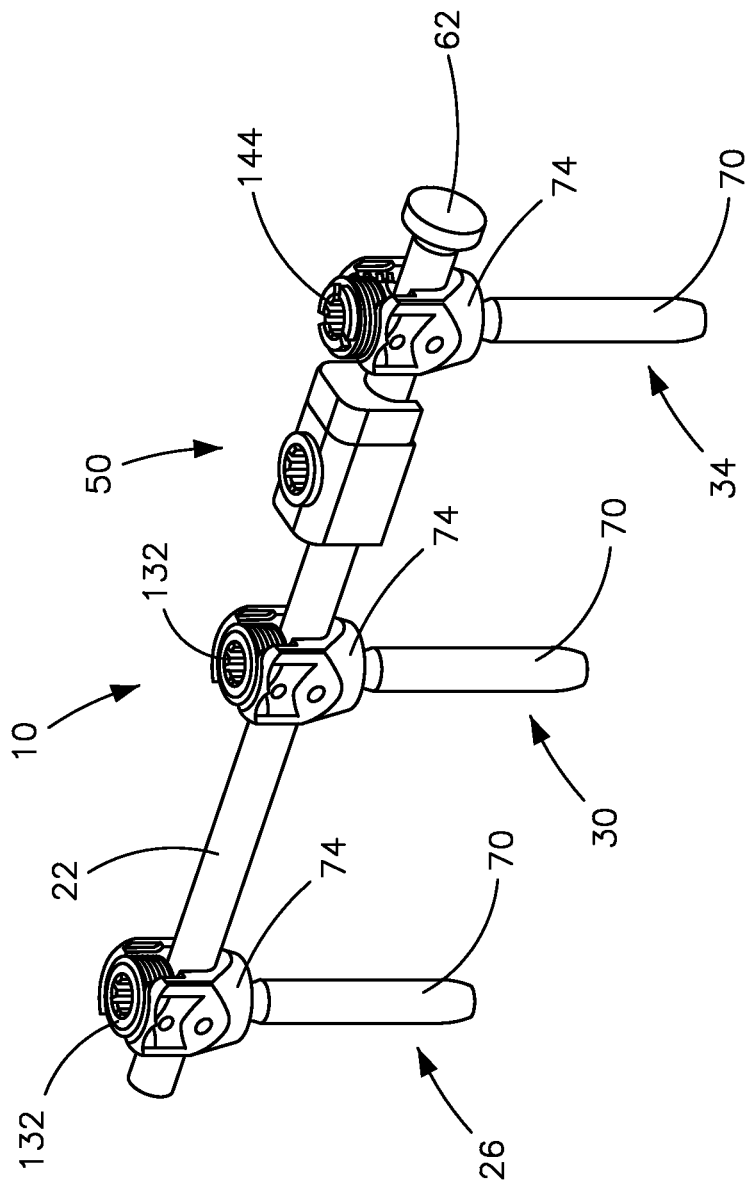
FIG. 5 is a perspective view of the dynamic stabilization system of FIG. 2 completely assembled.

In operation, and in reference to FIG. 5, a spinal rod and screw construct is assembled that spans both a fusion level and a non-fusion level using a spinal rod 22 and the pedicle screw assemblies 26, 30, and 34. At least one of the pedicle screw assemblies 26, 30, and 34 includes the two-step locking cap assembly 144, such as pedicle screw assembly 34, so that the spinal rod 22 is permitted to translate with respect to the pedicle screw assembly 34 while the angulation of the anchor portion 70 with respect to the pedicle screw assembly 34 is lockable as a result of the advancement of the outer locking screw 148 to cause the outer locking screw extension 160 to bear against the top of the collet 114 and cause the collet 114 to collapse around the head of anchor portion 70 while retaining the inner set screw 152 in a non-advanced state. A rigid construct characterizes the static fusion level, which may be a level in which an interbody spacer is positioned in the disc space and fusion is desired, while a dynamic construct characterizes the adjacent non-fusion level, where it is desirable to or reduce the occurrence adjacent level disease. The optional flare 62 of the rod 22 assists in preventing over translation of the spinal rod 22 with respect to pedicle screw assembly 34. The dynamic member 50 is preferably mounted to the spinal rod 22 adjacent the non-fusion level between the pedicle screw assemblies 30, and 34 by placing the member 50 over the spinal rod 22 and applying a downward force, which causes the collet 204 to expand and accept the spinal rod 22 in the channel 244 of the collet 204. The set screw 208 is advanced with respect to the body 200 and interacts with the threads on the collet 204, thereby causing the collet 204 to advance upwards with respect to the body 200, further causing the taper 228 of the legs of the body 200 to interact with the wider end portions 252 of the legs of the collet 204 and thereby force the distal portion of the collet 204 to collapse around the spinal rod 22 to lock the dynamic member 50 to the spinal rod 22. The elastomeric element 270 preferably serves as a bumper to one or both of the pedicle screw assemblies 30, and 34 during translation of the rod 22 with respect to pedicle screw assemblies 30, and 34. As shown, in FIG. 5, translation of rod 22 is limited to a distance T that is defined between elastomeric element 270 of member 50 and flare 62 of rod 22.

As a result of the inclusion of the two-step locking cap 144, any previously implanted pedicle screw and rod construct can be quickly adapted to provide dynamic stabilization to any desired level by loosening the inner set screw 152 to allow translational freedom of the spinal rod 22 with respect to any previously implanted pedicle screw assembly. The dynamic member 50 snaps over the rod 22 between any desired pair of pedicle screw assemblies 26, 30, and 34 to serve as a bumper and to limit overextension of the rod 22 with respect to any chosen pedicle screw assembly 26, 30, and 34. The dynamic member 50 can be provided in a range of sizes and can be coupled to any portion of the rod 22.

Figure 6:
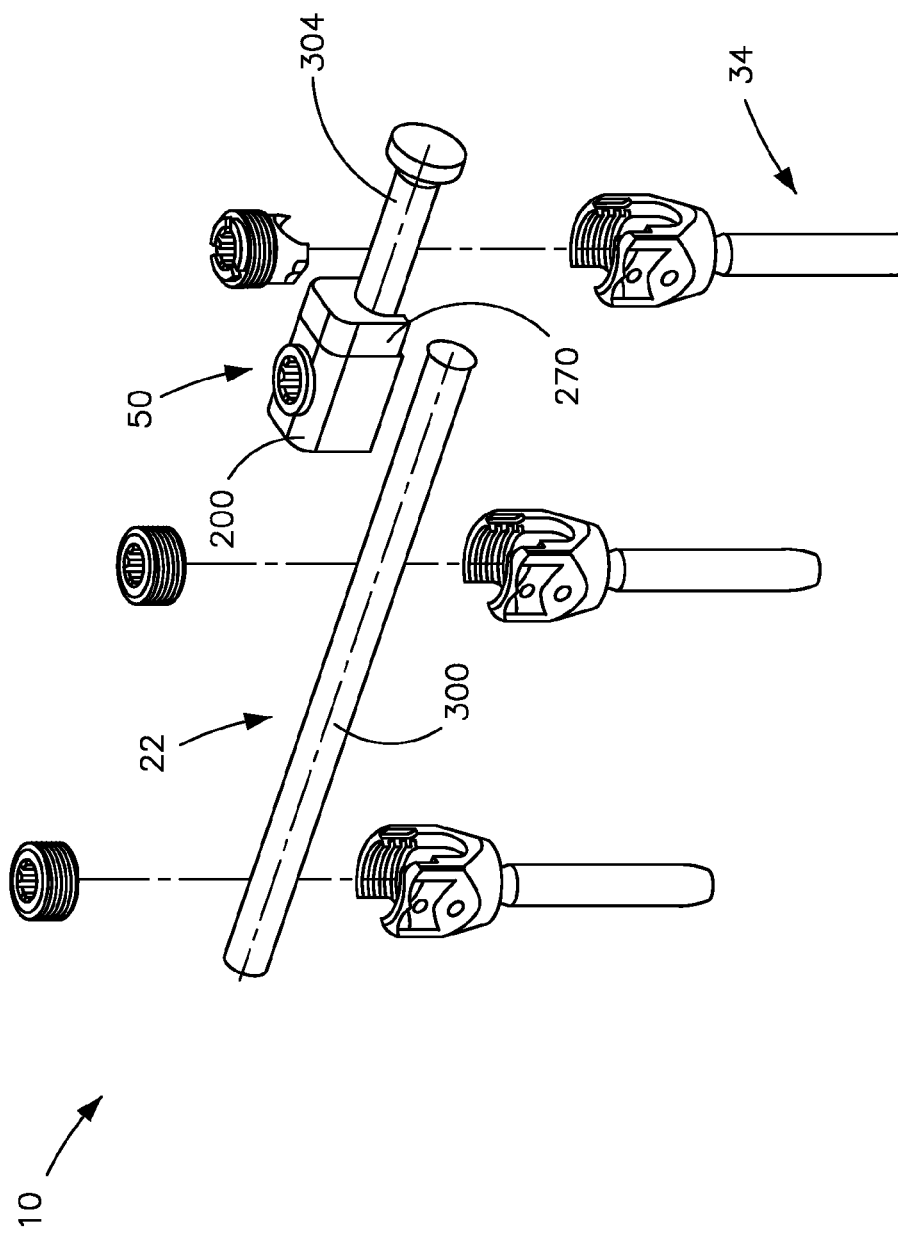
FIG. 6 is an exploded perspective view of a dynamic stabilization system according to another embodiment of the invention.

FIG. 6 shows another embodiment of the dynamic stabilization system 10. As shown, rod 22 may include a first portion 300, and a second portion 304 that is separate from the first portion 300. First portion 300 is configured to extend into body 200 of member 50 and is adapted to be connected to member 50 as described above. Second portion 304 extends from elastomeric portion 270 and is preferably integral therewith. For example, elastomeric portion 270 may be over-molded both body 200 and second portion 304. By having second portion 304 separate from first portion 300, rod 22 may not only be capable of translating with respect to pedicle screw assembly 34, but it also may be capable of flexing in all radial directions with respect to elastomeric element 270. Therefore, a patient will have additional mobility through the non-fusion level 18, as compared to a system having a single spinal rod 22, while the fusion level 14 is completely immobilized.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the present description.

What is claimed:

1. A dynamic stabilization system comprising:
    an elongated spinal rod having a diameter and a length along a first direction;
    a first and a second bone anchor each attached to the elongated spinal rod, wherein the first bone anchor is slidably attached to the spinal rod such that translational movement is permitted between the first bone anchor and the spinal rod along the first direction and the second bone anchor is attached to the spinal rod such that translational movement is not permitted between the second bone anchor and the spinal rod; and
    a dynamic member lockingly attached to the spinal rod and not connected to any other spinal rod or bone anchor at a position between the first and second bone anchors, comprising a body having a first and a second leg defining a body channel extending parallel to the spinal rod, a collet and an elastomeric stop member forming an end of the dynamic member located closer to the first bone anchor than the second bone anchor, the collet having a first and a second flexible leg defining therebetween a collet channel within which is located the spinal rod and a bottom opening wherein the first and second flexible legs of the collet can be adapted such that in a first position the bottom opening has a width greater than the diameter of the spinal rod and in a second position the width of the bottom opening is less than the diameter of the spinal rod.

2. The dynamic stabilization system of claim 1, wherein (i) the dynamic member further comprises a locking cap that extends through the body and into a bore defined by the collet, (ii) the bore of the collet has internal threads, (iii) the locking cap has external threads that engage the internal threads of the collet, and (iv) actuation of the locking cap tightens the collet around the spinal rod.

3. The dynamic stabilization system of claim 2, wherein the first and second legs of the body each have an inner surface that is tapered at a distal end, and each of the first and second flexible legs of the collet have an outer surface with a complementary taper to the tapered distal end of the inner surface of the first and second legs of the body.

4. The dynamic stabilization system of claim 1 wherein the dynamic member is positioned adjacent the first bone anchor such that the elastomeric stop member can limit the relative translational movement between the first bone anchor and the spinal rod in the first direction.

5. A dynamic stabilization system for stabilizing a first vertebral body with respect to a second vertebral body, comprising:
    a spinal rod having a diameter and a length along a first direction;
    a first bone anchor having a distal shaft fixedly secured to the first vertebral body and a second bone anchor having a distal shaft fixedly secured to the second vertebral body, the first bone anchor having an anchor seat attached to the spinal rod and can slide along the spinal rod such that translational movement is permitted between the first bone anchor and the spinal rod along the first direction while the anchor seat of the first bone anchor remains attached to the spinal rod, the second bone anchor having an anchor seat attached to the spinal rod such that translational movement is not permitted between the second bone anchor and the spinal rod; and
    a dynamic member lockingly attached to the spinal rod at a position between the first and second bone anchors, comprising a body having a first and a second leg defining a body channel extending parallel to the spinal rod, a collet and an elastomeric stop member forming an end of the dynamic member located closer to the first bone anchor than the second bone anchor, the collet having a first and a second flexible leg defining therebetween a collet channel within which is located the spinal rod and a bottom opening wherein the first and second flexible legs of the collet can be adapted such that in a first position the bottom opening has a width greater than the diameter of the spinal rod and in a second position the width of the bottom opening is less than the diameter of the spinal rod;
    wherein the dynamic member is not a component of any bone anchor assembly that is designed to be secured to any vertebral body and the dynamic member is not a component of a device that is designed to be attached to a second spinal rod;
    wherein the dynamic member is positioned on the spinal rod such that the elastomeric stop member can limit the translational movement in the first direction between the first bone anchor and the spinal rod.

6. The dynamic stabilization system of claim 5, wherein the spinal rod comprises a first portion and a second portion that is separate from and not integral with the first portion.

7. The dynamic stabilization system of claim 6, wherein (i) the first portion of the spinal rod is attached to the body of the dynamic member, and the second portion of the spinal rod is attached to the elastomeric stop member, and (ii) the elastomeric stop member is capable of flexing to thereby enable radial movement of the second portion of the spinal rod.

8. The dynamic stabilization system of claim 7, wherein the elastomeric stop member is over-molded onto the second portion of the spinal rod.

9. The dynamic stabilization system of claim 5, wherein the spinal rod has a first and a second end and the first end of the spinal rod includes a flange.

10. The dynamic stabilization system of claim 5, wherein (i) the dynamic member further comprises a locking cap that extends through the body and into a bore defined by the collet, (ii) the bore of the collet has internal threads, (iii) the locking cap has external threads that engage the internal threads of the collet, and (iv) actuation of the locking cap tightens the collet around the spinal rod.

11. The dynamic stabilization system of claim 10, wherein (i) each of the first and second legs of the body has an inner surface that is tapered at a distal end, and each of the first and second flexible legs of the collet has an outer surface with a complementary taper to the tapered distal end of the inner surface of the first and second legs of the body, and (ii) actuation of the locking cap causes the first and second legs of the body to collapse the first and second flexible legs of the collet together to clamp against the spinal rod.

12. The dynamic stabilization system of claim 5, wherein the first and second bone anchors are pedicle screws.

* * * * *